(12) United States Patent
Goren

(10) Patent No.: US 12,377,098 B2
(45) Date of Patent: Aug. 5, 2025

(54) COMPOSITIONS AND METHODS FOR THE TREATMENT OF ALOPECIA

(71) Applicant: Follea International, Irvine, CA (US)

(72) Inventor: Ofer A. Goren, Prague (CZ)

(73) Assignee: FOLLEA INTERNATIONAL, Irvine, CA (US)

( * ) Notice: Subject to any disclaimer, the term of this patent is extended or adjusted under 35 U.S.C. 154(b) by 0 days.

(21) Appl. No.: 18/295,476

(22) Filed: Apr. 4, 2023

(65) Prior Publication Data

US 2024/0277709 A1 Aug. 22, 2024

Related U.S. Application Data

(60) Provisional application No. 63/490,939, filed on Mar. 17, 2023, provisional application No. 63/488,045, filed on Mar. 2, 2023, provisional application No. 63/485,333, filed on Feb. 16, 2023.

(51) Int. Cl.
| | |
|---|---|
| *A61K 31/506* | (2006.01) |
| *A61K 9/20* | (2006.01) |
| *A61K 45/06* | (2006.01) |
| *A61P 17/00* | (2006.01) |

(52) U.S. Cl.
CPC ............... *A61K 31/506* (2013.01); *A61K 9/20* (2013.01); *A61K 45/06* (2013.01); *A61P 17/00* (2018.01)

(58) Field of Classification Search
CPC ........ A61K 31/506; A61K 9/20; A61K 45/06; A61P 17/00
See application file for complete search history.

(56) References Cited

U.S. PATENT DOCUMENTS

| | | | | |
|---|---|---|---|---|
| 10,633,688 | B2* | 4/2020 | Goren | C12Q 1/48 |
| 11,628,132 | B2* | 4/2023 | Goren | A61K 8/14 |
| | | | | 424/401 |
| 11,766,392 | B2* | 9/2023 | Goren | A61K 8/361 |
| | | | | 424/401 |
| 2003/0170331 | A1* | 9/2003 | Cals-Grierson | A61P 17/10 |
| | | | | 424/769 |
| 2020/0214958 | A1 | 7/2020 | Goren et al. | |
| 2021/0059920 | A1* | 3/2021 | Goren | A61K 9/5115 |
| 2022/0296486 | A1* | 9/2022 | Goren | A61K 8/4953 |

OTHER PUBLICATIONS

Supikova, K.; Kosinova, A.; et al. "Sulfated phenolic acids in plants" Planta. May 13, 2022;255(6):124. (Year: 2022).*
International Search Report and Written Opinion for PCT/US2023/017414 filed Apr. 4, 2023, dated Nov. 6, 2023.

* cited by examiner

*Primary Examiner* — Andrew D Kosar
*Assistant Examiner* — John D McAnany
(74) *Attorney, Agent, or Firm* — Buchanan Ingersoll & Rooney PC

(57) ABSTRACT

Embodiments relate to compositions and methods for the treatment of hair loss, which can include treatment of alopecia, via an application of a composition including an alkalizing agent and/or a sulfotransferase enzyme. The composition can be formulated to be an orally administered composition. In some embodiments, the composition is used to increase the response of minoxidil.

13 Claims, No Drawings

COMPOSITIONS AND METHODS FOR THE TREATMENT OF ALOPECIA

CROSS-REFERENCE TO RELATED APPLICATIONS

This patent application is related to and claims the benefit of priority to U.S. provisional patent application No. 63/490,939 filed on Mar. 17, 2023, U.S. provisional patent application No. 63/489,499 filed on Mar. 10, 2023, U.S. provisional patent application No. 63/488,045 filed on Mar. 2, 2023, and U.S. provisional patent application No. 63/485,333 filed on Feb. 16, 2023, the entire contents of each are incorporated by reference.

FIELD OF THE INVENTION

Embodiments can relate to compositions and methods for the treatment of hair loss, which can include treatment of alopecia, via an application of a composition including an alkalizing agent and/or a sulfotransferase enzyme. The composition can be formulated to be an orally administered composition. In some embodiments, the composition is used to increase the response of minoxidil.

BACKGROUND OF THE INVENTION

A drug that can be used for the treatment of alopecia is minoxidil. In order for minoxidil to exert its hair growth properties, minoxidil must be activated by the SULT1A1 (minoxidil sulfotransferase) enzyme. The enzyme is expressed both in the scalp and the liver. Different people express different amount of the enzyme or possess genetic variations that effect the activity of the enzyme; thus, the response to minoxidil treatment is variable among people and dependent on the SULT1A1 enzyme.

Previous research demonstrated that alkalinizing the intracellular pH of keratinocytes induces the expression of SULT1A1 enzyme in the scalp and subsequently improves, increases, or enhances minoxidil response. Accordingly, a topical alkalizing agent was developed as a minoxidil booster; however, this topical minoxidil booster was met with limited success since it is difficult to comply with twice daily applications, it tends to change hair color, and it tends to leave residue from sodium bicarbonate on the hair. Further, minoxidil exerts its hair re-growth effect mainly through the dermal papillae and dermal sheath cells which are difficult to treat with topical cosmetic products.

The dermal papillae have a rich blood supply, which can make it easier to modulate with orally administered compositions (e.g., drugs, ingredients, supplements, etc.). As such, an oral composition that increases SULT1A1 enzyme in dermal papillae, dermal sheath, or outer root sheath of hair follicles and subsequently increases the response to minoxidil (which can be oral or topological) for the treatment of hair loss would be advantageous.

Prior to this present disclosure, it was not known as to whether an oral form of an alkalizing agent would be able induce the SULT1A1 enzyme in the scalp tissue. In addition, as it is known that patients chronically using large dosages of an oral alkalizing agent could develop metabolic alkalosis and other disorders, the negative effects of an oral form of an alkalizing agent were not know. The inventor has conducted a study to test these effects, the result of which are the basis of the innovations disclosed herein.

SUMMARY OF THE INVENTION

Embodiments relate to compositions and methods for the treatment of hair loss, which can include treatment of alopecia, via an application of a composition including an alkalizing agent and/or a sulfotransferase enzyme. The composition can be formulated to be an orally administered composition. In some embodiments, the composition is used to increase the response of minoxidil.

An exemplary embodiment can relate to a composition for improving, increasing, or enhancing minoxidil response of a subject suffering from alopecia. The composition can include an alkalizing agent and a sulfotransferase enzyme.

In some embodiments, the composition can be formulated as a topological composition, an oral composition, an injectable composition, or a transdermal composition; and/or the composition can be formulated as a drug, a nutritional supplement, or a cosmetic.

In some embodiments, the composition can include minoxidil.

In some embodiments, the composition can include minoxidil. The composition can be formulated as a topological composition, an oral composition, an injectable composition, or a transdermal composition.

In some embodiments, the alkalizing agent can include one or more of a bicarbonate, citrate, a loop diuretic, MOPS, BES, TES, HEPES, DIPSO, TAPSO, Acetamidoglycine, POPSO, HEPPSO, HEPPS, Tricine, Tris (tromethamine), Glycinamide, Glycylglycine, or Bicine, TAPS.

In some embodiments, the sulfotransferase enzyme can include a human sulfotransferase enzyme and/or a non-human sulfotransferase enzyme.

In some embodiments, the sulfotransferase enzyme can include one or more of a carbohydrate sulfotransferase, a galactose-3-O-sulfotransferase, a heparan sulfate 2-O-sulfotransferase, a heparan sulfate 3-O-sulfotransferase, a heparan sulfate 6-O-sulfotransferase, a N-deacetylase/N-sulfotransferase, a tyrosylprotein sulfotransferase, an uronyl-2-sulfotransferase, an estrone sulfotransferase, a chondroitin 4-sulfotransferase, SULT1A1, SULT1A2, SULT1A3, SULT1A4, SULT1B1, SULT1C2, SULT1C3, SULT1C4, SULT1D1P, SULT1E1, SULT2A1, SULT2B1, SULT4A1, or SULT6B1.

In some embodiments, the composition can contain natural levels or extracts of minoxidil sulfotransferase enzymes, natural levels or extracts of phenol sulfotransferase enzymes, and/or natural levels or extracts of sulfotransferase enzymes derived from *Populus trichocarpa, Populus* x *canescens, Salix* sp., *Arabidopsis thaliana*, silver poplar (*Populus alba*), Simon's poplar (*Populus simonii*), *S. purpurea, P. tremuloides, I. polycarpa, P. nigra, Oryza sativa*, Salicaceae family, Poplars (*Populus* sp.), *Idesia polycarpa*-Japanese orange cherry, Potato (*Solanum tuberosum*), Cabbage (*Brassica rapa*), *Populus trichocarpa* (Black cottonwood), *Salix* Sp. (Willow tree), Cotton (*Gossypium*), *Olea europaea* L, *Brassica napus, Apium graveolens, Brassica oleracea, Saccharina japonica, Solanum tuberosum*, and/or Black cottonwood. The natural levels or extracts of minoxidil sulfotransferase enzymes, phenol sulfotransferase enzymes, and/or sulfotransferase enzymes is/are present in amounts ranging from 1%-100% by weight.

In some embodiments, the sulfotransferase enzyme can includeOeST1.

An exemplary embodiment can relate to a method for improving, increasing, or enhancing minoxidil response of a subject suffering from alopecia. The method can involve administering a composition comprising an alkalizing agent and a sulfotransferase enzyme to a subject suffering from alopecia.

In some embodiments, administering the composition can involve administering the composition topologically, orally, via injection, or transdermally; and/or administering the composition as a drug, a nutritional supplement, or a cosmetic.

In some embodiments, the method can involve administering the composition before, during, and/or after administration of minoxidil.

In some embodiments, the composition can include minoxidil.

In some embodiments, the alkalizing agent can include one or more of a bicarbonate, citrate, a loop diuretic, MOPS, BES, TES, HEPES, DIPSO, TAPSO, Acetamidoglycine, POPSO, HEPPSO, HEPPS, Tricine, Tris (tromethamine), Glycinamide, Glycylglycine, or Bicine, TAPS.

In some embodiments, the sulfotransferase enzyme can include a human sulfotransferase enzyme and/or a non-human sulfotransferase enzyme.

In some embodiments, the sulfotransferase enzyme can include one or more of a carbohydrate sulfotransferase, a galactose-3-O-sulfotransferase, a heparan sulfate 2-O-sulfotransferase, a heparan sulfate 3-O-sulfotransferase, a heparan sulfate 6-O-sulfotransferase, a N-deacetylase/N-sulfotransferase, a tyrosylprotein sulfotransferase, an uronyl-2-sulfotransferase, an estrone sulfotransferase, a chondroitin 4-sulfotransferase, SULT1A1, SULT1A2, SULT1A3, SULT1A4, SULT1B1, SULT1C2, SULT1C3, SULT1C4, SULT1D1P, SULT1E1, SULT2A1, SULT2B1, SULT4A1, or SULT6B1.

In some embodiments, the composition contains natural levels or extracts of minoxidil sulfotransferase enzymes, natural levels or extracts of phenol sulfotransferase enzymes, and/or natural levels or extracts sulfotransferase enzymes derived from *Populus trichocarpa, Populus* x *canescens, Salix* sp., *Arabidopsis thaliana*, silver poplar (*Populus alba*), Simon's poplar (*Populus simonii*), *S. purpurea, P. tremuloides, I. polycarpa, P. nigra, Oryza sativa*, Salicaceae family, Poplars (*Populus* sp.), *Idesia polycarpa*-Japanese orange cherry, Potato (*Solanum tuberosum*), Cabbage (*Brassica rapa*), *Populus trichocarpa* (Black cottonwood), *Salix* Sp. (Willow tree), Cotton (*Gossypium*), *Olea europaea* L, *Brassica napus, Apium graveolens, Brassica oleracea, Saccharina japonica, Solanum tuberosum*, and/or Black cottonwood. The natural levels or extracts of minoxidil sulfotransferase enzymes, phenol sulfotransferase enzymes, and/or sulfotransferase enzymes is/are present in amounts ranging from 1%-100% by weight.

In some embodiments, the sulfotransferase enzyme can include OeST1.

In some embodiments, the method can involve quantifying activity of SULT1A1 in dermal papillae cells and/or dermal sheath of the subject.

In some embodiments, the method can involve determining a therapy treatment using the composition based on the quantitative measurement of activity of SULT1A1 in dermal papillae cells and/or dermal sheath of the subject.

An exemplary embodiment can relate to a composition for increasing sulfotransferase enzyme activity in a scalp and/or a liver of a subject suffering from alopecia. The composition can include an alkalizing agent and a sulfotransferase enzyme.

An exemplary embodiment can relate to a method for increasing sulfotransferase enzyme activity in a scalp and/or a liver of a subject suffering from alopecia. The method can involve administering a composition comprising an alkalizing agent and a sulfotransferase enzyme to a subject suffering from alopecia.

As used herein, the terms "prevent" or "prevention" and other derivatives of the words, when used in reference to alopecia, e.g., androgenetic alopecia, can refer to a reduced likelihood of alopecia in an individual receiving a given treatment relative to that of a similar individual at risk for alopecia but not receiving that treatment. As such, the terms "prevent" and "prevention" can encompass a treatment that results in a lesser degree of alopecia than would be otherwise expected for a given individual. Efficacy for prevention of alopecia can be established through controlled studies, e.g., in which a subject is administered a treatment (e.g., a topical, oral, transdermal, etc.) and another subject is administered a placebo. Under these circumstances, if the subject treated with the treatment undergoes less hair loss over time relative to the subject receiving the placebo, e.g., at least 5% less, at least 10% less, at least 15% less, at least 20% less, at least 25% less, at least 30% less, at least 35% less, at least 40% less, at least 45% less, at least 50% less or beyond, the treatment can be considered effective for the prevention of alopecia.

As used herein, the term "subject" refers to a human or animal in need of a therapeutic treatment for androgenetic alopecia or any other form of alopecia.

As used herein, the terms "treat," "treatment," or "treating" refer to therapeutic treatments, wherein the object is to reverse, alleviate, ameliorate, inhibit, slow down or stop the progression or severity of a disease or condition, e.g., androgenetic alopecia or other form of alopecia. The term "treating" can include reducing or alleviating at least one adverse effect or symptom of the disease or condition. Treatment can be considered to be generally "effective" if one or more symptoms are reduced. Alternatively, treatment can be "effective" if the progression of a disease is reduced or halted. That is, "treatment" can include not just the improvement of symptoms, but also a cessation of, or at least slowing of, progress or worsening of symptoms compared to what would be expected in the absence of treatment. Beneficial or desired clinical results can include, but are not limited to, alleviation of one or more symptom(s), diminishment of extent of disease, stabilized (e.g., not worsening) state of disease, delay or slowing of disease progression, amelioration or palliation of the disease state, remission (whether partial or total), and/or decreased mortality. For example, treatment can be considered effective if the extent or amount of hair loss is reduced, or the progression of hair loss is slowed or halted. The term "treatment" of a disease can also include providing relief from the symptoms or side-effects of the disease (including palliative treatment).

Efficacy of treatment to treat or prevent alopecia can be determined by monitoring the density of hairs on a given area of the subject's body, e.g., a given area of the scalp. For example, if the rate of hair loss is reduced, e.g., by 10% or more following treatment, the treatment can be considered effective for the prevention of alopecia. Similarly, if hair density remains the same, the treatment can be considered to be effective for the prevention of alopecia. If the density of hair increases, e.g., by 5% or more, e.g., by 10% or more following treatment, the treatment can also be considered effective for the treatment and/or prevention of androgenetic alopecia. Efficacy of treatment to treat or prevent androgenetic alopecia can be determined by monitoring global photography. For example, the patient or an expert can assess the treatment response utilizing before and after global photographs.

As used herein the term "alopecia" refers to all forms of hair loss in humans or animals, both male and female, including but not limited to traction alopecia, androgenetic alopecia, male pattern baldness, female pattern hair loss, alopecia areata, alopecia universalis, telogen effluvium, chemotherapy induced alopecia, hair shedding, eyebrow hair loss, beard hair loss, hair thinning, etc. The term permits the presence of elements that do not materially affect the basic and novel or functional characteristic(s) of that embodiment.

To utilize the compositions described herein, subject can apply an effective amount of the composition to the scalp. The term "effective amount," as used herein, can be an amount which is effective in preventing or treating hair loss.

Further features, aspects, objects, advantages, and possible applications of the present invention will become apparent from a study of the exemplary embodiments and examples described below, in combination with the FIGURES, and the appended claims.

DETAILED DESCRIPTION OF THE INVENTION

The following description is of exemplary embodiments that are presently contemplated for carrying out the present invention. This description is not to be taken in a limiting sense, but is made merely for the purpose of describing the general principles and features of the present invention. The scope of the present invention is not limited by this description.

Alopecia, and in particular androgenetic alopecia, is the progressive miniaturization of hair follicles on the female scalp. It can be characterized by diffuse thinning of the crown region of the scalp while the frontal hairline remains intact. Alopecia is generally hereditary, but can also dependent on hormones that may influence its development. Oral and/or topical minoxidil an U.S. FDA approved drug for the treatment of alopecia. Its use can provide a moderate increase in hair regrowth. The risk for adverse events with such minoxidil use is low; however, irritant dermatitis, allergic contact dermatitis, and hypertrichosis have been reported.

Embodiments can relate to compositions and methods for treating alopecia. For example, a composition can be administered to induce the SULT1A1 enzyme. The composition can be formulated as a topological composition, an oral composition, an injectable composition, a transdermal composition, etc. In some embodiments, the composition can be formulated and/or administered to induce the scalp SULT1A1 enzyme. In some embodiments, the composition can be formulated and/or administered to increase minoxidil response in a subject suffering from alopecia. As will be explained herein, inducing SULT1A1 enzyme (which improves, increases, or enhances minoxidil response) can be achieved by the composition including an alkalizing agent and/or a sulfotransferase enzyme (e.g., an enzyme supplement extracted from plants, bacteria, animals, fungi, etc.).

While embodiments disclosed herein may specifically discuss treatment of a form of alopecia (e.g., androgenetic alopecia), it is understood that the compositions and methods disclosed can be similarly applicable for treatment of other forms of alopecia.

The composition can be administered with or without minoxidil treatment. The minoxidil treatment can be a treatment involving administration of a composition containing minoxidil, the minoxidil composition being a topological composition, an oral composition, an injectable composition, a transdermal composition, etc. If the composition is administered with the minoxidil treatment, the composition can be administered before the minoxidil treatment (e.g., before the minoxidil composition is administered), during the minoxidil treatment (e.g., while the minoxidil composition is administered), and/or after the minoxidil treatment (e.g., after the minoxidil composition is administered). This can include administering the composition and the minoxidil at the same time, each administered on the same day but at different times, etc. In some embodiments, the composition (e.g., the composition having the alkalizing agent and/or the sulfotransferase enzyme) can include the minoxidil. In some embodiments, the composition does not include minoxidil but the composition and the minoxidil are administered together as part of the treatment.

The minoxidil composition or minoxidil ingredient of a composition can be minoxidil or a pharmaceutically acceptable salt thereof. Minoxidil is a pro-drug converted to its active form, minoxidil sulfate, by sulfotransferase enzymes present in the outer root sheath (ORS) of hair follicles (See Buhl A E, Waldon D J, Baker C A, Johnson G A. Minoxidil sulfate is the active metabolite that stimulates hair follicles. J Invest Dermatol. 1990 November; 95(5):553-7). It has been demonstrated that the activity of sulfotransferase in the ORS determines the clinical response to minoxidil (See Goren A, Castano J A, McCoy J, Bermudez F, Lotti T. Novel enzymatic assay predicts minoxidil response in the treatment of androgenetic alopecia. Dermatol Ther. 2014; 27(3): 171-3). It is contemplated for the minoxidil concentration to be about 2 to about 20% by weight. However, other concentrations can be used.

Minoxidil induces (up-regulates) the expression of sulfotransferases in hair bearing skin, hair follicles, and/or keratinocyte cells, e.g., the scalp. This can include up-regulating the sulfonating capacity. Embodiments of the compositions and methods disclosed herein can also induce the expression of sulfotransferases. However, embodiments of the compositions can also improve, increase, or enhance the subject's response to minoxidil in this regard—e.g., compositions can increase the rate, the amount, the duration, the effect, etc. of up-regulation of expression of sulfotransferases in hair bearing skin, hair follicles, and/or keratinocyte cells. For example, embodiments of the methods and compositions disclosed herein can be used to increase the metabolism of minoxidil (which can result in the increase of bioavailable minoxidil sulfate) in hair follicles of subjects suffering from a form of alopecia.

Any of the treatments disclosed herein can be administered at a predetermined frequency. This predetermined frequency can be once every 24 hours, twice every 24 hours, three times every 24 hours, four times every 24 hours, etc. For instance, the composition can be formulated to be administered twice every 24 hours. Again, the treatment can involve use of the composition alone, or use of the composition with a separate administration of minoxidil. Thus, the treatment can involve administering minoxidil at a predetermined frequency. The composition administration frequency can be the same or different from the minoxidil administration frequency. In some embodiments, the composition itself includes minoxidil.

Any of the compositions disclosed herein can be an oral formulation, a topological formulation, an injectable formulation, a transdermal formulation, etc. Any or the oral formulations disclosed herein can be in tablet form, pill form, capsule form, gel form, liquid form, spray form, etc. Any of the oral formulations or any one or combination of ingredients of the oral formulation can be in dry, wet, lypolized, etc. Any of the topological formulations disclosed herein can be a lotion, an ointment, a shampoo (wet or dry), an aerosol for application as a foam or mousse, a liquid solution, a gel, etc. These can be mediums applied to the scalp, for example. Any of the topological formulations or any one or combination of ingredients of the topological formulation can be in dry, wet, lypolized, etc. Any of the injectable formulations disclosed herein can be in intradermal injection form. Any of the injectable formulations or any one or combination of ingredients of the injectable formulation can be in dry, wet, lypolized, etc. Any of the transdermal formulations disclosed herein can be in the form of controlled release vehicle, such as a patch for example. Any of the transdermal formulations or any one or combination of ingredients of the transdermal formulation can be in dry, wet, lypolized, etc.

It is contemplated for the compositions disclosed herein to be formulated as a cosmetic (e.g., lotion, ointment, shampoo (wet or dry), aerosol for application as a foam, mousse, or hairspray, a liquid solution, a gel, etc. However, any of the compositions disclosed herein can be formulated in the form of a drug, a nutritional supplement, cosmetic product, etc.

Depending on the use and implementation, any of the topological formulations can include a solvent. The solvent may or may not be volatile. The solvent can be an alcohol, such as a polyhydric alcohol, benzyl alcohol, propylene glycol, water, et. Any of the topological formulations can include a starch (modified or unmodified starch). It is contemplated for the starch to act as a sebum absorber. Non-limiting examples of suitable unmodified starch materials can include cornstarch, potato starch, tapioca starch, rice starch, wheat starch, cassaya starch, etc. A modified starch material is a starch which has been derivatized or altered by processes known to those of ordinary skill in the art, such as esterification, etherification, oxidation, acid hydrolysis, crosslinking, enzyme conversion, etc. Non-limiting examples of suitable modified starch materials include aluminum starch octenylsuccinate, sodium starch octenylsuccinate, calcium starch octenylsuccinate, distarch phosphate, hydroxyethyl starch phosphate, hydroxypropyl starch phosphate, sodium carboxymethyl starch, and sodium starch glycolate. Any of the topological formulations can include oil-absorbing agent and/or suspending agent, such as silica, cellulose, chalk, talc, fuller's earth, etc. Some embodiments can include other sebum absorbers, such as a clay material, which may be stearalkonium hectorite, stearalkonium bentonite, quaternium-18 bentonite, quaternium-18 hectorite, etc. Use of a sebum absorber, oil-absorbing agent, suspending agent can facilitate a more pleasing aesthetic to a user when minoxidil is administered by reducing or eliminating an oily and/or unaesthetic appearance of hair.

Any of the topological formulations can include embodiments of the composition formulated as a dry shampoo. By "dry shampoo," it is meant that the composition is formulated to include a carrier material that is a volatile liquid and therefore evaporates and a powder that remains, wherein the powder contains a starch. An exemplary starch can be aluminum starch octenyl succinate. Examples of suitable carrier materials that are volatile liquids can be lower alcohols including without limitation ethanol or isopropanol, a volatile silicone compound such as polydimethylsiloxanes (e.g., having a viscosity less than about 5 cSt at 25° C.), cyclomethicone, cyclohexane siloxane, decamethyltetrasiloxane, octamethyltrisiloxane, decamethylpentasiloxane, decamethylcyclopentasiloxane, octamethylcyclotetrasiloxane, trimethylsilylamodimethicone, phenyl trimethicone, hexamethyidisiloxane, dimethylsiloxane/methylalkylsiloxane, etc. Other carrier materials known to those skilled in the art may also be used. Use of a dry shampoo may be preferred in some instances because dry shampoo tends to not wash away the minoxidil—embodiments of the composition are intended to be used with minoxidil treatment. The minoxidil itself may be formulated as a dry shampoo.

Any of the topological formulations can include embodiments of the composition formulated as a spray, aerosol, etc. In this regard, any of the topological formulations can be a composition including a propellant (e.g., butane, isobutane, propane, A-46 (isobutane and propane), liquefied petroleum gas (e.g., propane), dimethyl ether, methyl ethyl ether, trichlorofluoromethane, dichlorodifluoromethane, dichlorotetrafluorothane, monochlorodifluoromethane, trichlorotrifluoroethane propane, carbon dioxide, nitrous oxide, 1,1,1,2,-tetrafluoroethane, 1,1,2,3,3,3-heptafluoropropane, etc.). A propellant may condense to a liquid state in an aerosol container at ambient temperatures. In some embodiments, the propellant may have a lower specific gravity as compared to the rest of the composition, thus facilitating propelling the composition from a container (e.g., through a dip tube) as compared to expelling the propellant.

Depending on the use and implementation, any of the formulations can be a composition including a carrier. For instance, any of the formulations can be encapsulated in a pharmaceutically acceptable carrier. The pharmaceutically acceptable carrier can encapsulate the composition in liposomes, microbeads, etc. In addition to being "pharmaceutically acceptable," each carrier can be "acceptable" in the sense of being compatible with the other ingredients of the formulation. The carrier can be used to temporarily encapsulate the composition until a condition is met that causes its release. In some embodiments, the carrier can be formulated to controllably release the composition—e.g., a time-dependent release.

Depending on the use and implementation, any of the formulations can be a composition including a penetration enhancer. The penetration enhancer can enhance penetration of the composition and/or minoxidil in the skin (e.g., the scalp). Suitable penetrating enhancer agents can include alcohols (e.g., dodecanol, oleyl alcohol, etc.); amines (e.g., isopropyl amine, diisopropyl amine, triethyl amine, triethanol amine, diisopropanolamine, ethylene diamine, etc.); carboxylic acids (e.g., oleic acid, linoleic acid, linolenic acid, etc.); esters (e.g., dibutyl sebacate, dibutyl phthalate, butyl benzoate, ethyl caprate, etc.); Azone, N methyl pyrollidone; bile salts; urea; glycols (e.g., diethylene glycol and tetraethylene glycol); fatty acids (e.g., lauric acid, myristic acid and capric acid); fatty esters; fatty ethers; cyclodextrines; occlusive agents; surface active agents; dimethylaminopropionic acid derivatives; terpenes; sulfoxides; cyclic ethers; amides; sulphoxides (e.g., dimethylsulphoxide, DMSO, decylmethalsulfoxide, etc.); Azones (e.g., 1-dodecylazacycloheptan-2-one, laurocapran, laurocapram); pyrrolidones (e.g., 2-pyrrolidone, 2P, N-methylpyrrilidone, N-methyl-2-pyrrolidone, NMP, 1-propyl-3-dodecyl-2-pyrrolidone, 1-butyl-3-dodecyl-2-pyrrolidone, etc.); surfactants (e.g., polyoxyethylene-2-oleyl ether, polyoxy ethylene-2-stearly ether, sodium dodecyl sulfate, SDS, sodium lauryl sulfate, SLS); oxazolidinones (e.g., 4-decyloxazolidin-2-one), urea, 2-(1-nonyl)-1,3-dioxolane; terpenes; polyester nanosponges; liposomes; phospholipids; cyclopentadecalactone; pentadecalactone; SNAC; salcaprozate sodium Sodium N-[8-(2-hydroxybenzoyl) amino]caprylate; CNAC; 5-CNAC; 8-(N-2-hydroxy-5-chloro-benzyl)-amino-caprylic acid; sodium caprate; glyceryl triglyceride; peptides; etc.

Depending on the use and implementation, any of the formulations can be a composition including an exfoliating agent to promote abrasion of the surface of the skin (e.g., surface of the scalp) and/or promote absorption of a composition and/or an ingredient of a composition. Examples of exfoliating agents can include (1) inorganic and/or metallic particles such as: boron nitride, in body-centered cubic form (Borazon®); aluminosilicate (e.g. nepheline); zircon; mixed oxides of aluminum such as emery; zinc oxide; aluminum oxides such as aluminas or corundum; titanium oxide; titanium oxide coated mica; carbides, in particular silicon carbide (carborundum); or other metal oxides; metals, and metal alloys such as iron shot, steel shot, and in particular perlite; silicates such as glass, quartz, sand, or vermiculite; calcium carbonate (e.g. Bora-Bora sand or Rose de Brignoles sand) or magnesium carbonate; sodium chloride; pumice stone; amorphous silica; diamond; ceramics, (2) organic particles such as: fruit stones, in particular apricot stones, e.g. Scrubami® apricot; wood cellulose, e.g. ground bamboo stem; coconut shell, e.g. coconut exfoliator; polyamides, in particular Nylon-6; sugars; plastic microbeads, e.g. polyethylenes or polypropylenes; ground walnut; ground apricot seed; ground shells, (3) mixed particles associating organic and inorganic compounds, particles coated in the compounds identified above, etc.

Depending on the use and implementation, any of the formulations can be a composition incorporated into a controlled release vehicle (e.g., an encapsulation) that would allow an ingredient or agent of the composition to be controllably released into the dermis of the skin (e.g., scalp). Capsules or vehicles that encapsulate the ingredient or agent can include, but are not limited to, liposomes, non-ionic liposomes, niosomes, novasome I, erythromycin-Zn complex, microspheres, nanoparticles, solid lipid nanoparticles, and nanoemulsions.

Embodiments of the treatment can involve the use of one or more compositions. The composition can include one or more alkalizing agents. For instance, the treatment might involve administering composition-1 and composition-2, wherein composition-1 has an alkalizing agent that differs from an alkalizing agent used in composition-2. In addition, one composition might have the same alkalizing agent(s) as another composition, but the concentration or amounts of alkalizing agents may differ. In addition, one composition might be administered before administration of minoxidil, while the other might be administered after administration of minoxidil. As explained herein, some compositions can be formulated with penetration agents, carrier material, etc. The compositions used in the treatment might also differ based on the inclusion of these ingredients. How many compositions to use, how many alkalizing agents to use, when to administer them, if/when to use them with minoxidil can be determined based on desired effects and/or design criteria.

Embodiments of the composition can include one or more alkalizing agents. Any of the alkalizing agents can include a bicarbonate or a combination of bicarbonates. Examples of bicarbonates can include sodium bicarbonate, potassium bicarbonate, magnesium bicarbonate, calcium bicarbonate, etc. Other alkalizing agents can include a citrate or a combination of citrates. Examples of citrates can include potassium citrate, sodium citrate, citric acid, etc. Other alkalizing agents can include a loop diuretic or a combination of loop diuretics. Examples of loop diuretics can include Bumetanide (Bumex), Ethacrynic acid (Edecrin), Furosemide (Lasix), Torsemide (Soaanz), etc. Other alkalizing agents can include MOPS, BES, TES, HEPES, DIPSO, TAPSO, Acetamidoglycine, POPSO, HEPPSO, HEPPS, Tricine, Tris (tromethamine), Glycinamide, Glycylglycine, Bicine, TAPS, etc.

Embodiments of the composition can include one or more sulfotransferase enzymes. Any of the sulfotransferase enzymes can be human or non-human. Examples of a sulfotransferase enzyme can be a carbohydrate sulfotransferase (e.g., CHST1, CHST2, CHST3, CHST4, CHST5, CHST6, CHST7, CHST8, CHST9, CHST10, CHST11, CHST12, CHST13, CHST14, etc.), a galactose-3-O-sulfotransferase (e.g., GAL3ST1, GAL3ST2, GAL3ST3, GAL3ST4, etc.), a heparan sulfate 2-O-sulfotransferase (e.g., HS2ST1), a heparan sulfate 3-O-sulfotransferase (e.g., HS3ST1, HS3ST2, HS3ST3A1, HS3ST3B1, HS3ST4, HS3ST5, HS3ST6, etc.), a heparan sulfate 6-O-sulfotransferase (e.g., HS6ST1, HS6ST2, HS6ST3, etc.), a N-deacetylase/N-sulfotransferase (e.g., NDST1, NDST2, NDST3, NDST4, etc.), a tyrosylprotein sulfotransferase (e.g., TPST1, TPST2, etc.), an uronyl-2-sulfotransferase, an estrone sulfotransferase, a chondroitin 4-sulfotransferase, SULT1A1, SULT1A2, SULT1A3, SULT1A4, SULT1B1, SULT1C2, SULT1C3, SULT1C4, SULT1D1P, SULT1E1, SULT2A1, SULT2B1, SULT4A1, SULT6B1, etc.

In an exemplary embodiment, the sulfotransferase enzyme can be a phenol sulfotransferase extract (e.g., phenol sulfotransferase extracted from a plant producing a sulfated salicinoid). Examples of plants producing sulfated salicinoids can include *Populus trichocarpa, Populus x canescens, Salix* sp., *Arabidopsis thaliana*, silver poplar (*Populus alba*), Simon's poplar (*Populus simonii*), *S. purpurea, P. tremuloides, I. polycarpa, P. nigra, Oryza sativa*, Salicaceae family, Poplars (*Populus* sp.), *Idesia polycarpa*-Japanese orange cherry, Potato (*Solanum tuberosum*), Cabbage (*Brassica rapa*), *Populus trichocarpa* (Black cottonwood), *Salix* Sp. (Willow tree), Cotton (*Gossypium*), *Olea europaea* L, *Brassica napus, Apium graveolens, Brassica oleracea, Saccharina japonica, Solanum tuberosum*, Black cottonwood, etc.

In another exemplary embodiment, the sulfotransferase enzyme can be OeST1 (olive tree SULT1A1). OeST1 is a sulfotransferase plant supplement that can be extracted from olive trees. The human homolog of OeST1 is SULT1A1, which belongs to the cytosolic sulfotransferase family. Like OeST1, SULT1A1 catalyzes the transfer of a sulfonate group from PAPS to the hydroxyl group of various phenolic substrates, including flavonoids, catecholamines, and xenobiotics. The expression level of OeST1 can vary depending on the tissue, developmental stage, and environmental conditions of the olive plant. However, studies have shown that OeST1 is most abundant in the fruit and leaves of olive. In olive fruit, OeST1 is expressed at high levels during the early stages of development and ripening, when flavonoids and other phenolic compounds are synthesized and accumulated. The expression of OeST1 in olive fruit is regulated by various factors, including light, temperature, and water availability, which can affect the synthesis and accumulation of flavonoids and other phenolics in the fruit. In olive leaves, OeST1 is also expressed at high levels, particularly in young and actively growing leaves. The expression of OeST1 in olive leaves is regulated by various factors, including light, temperature, and biotic and abiotic stresses, which can affect the biosynthesis and accumulation of flavonoids and other phenolics in the leaves. Overall, the expression of OeST1 in olive fruit and leaves suggests that sulfated flavonoids and other phenolics may play important roles in the physiology and adaptation of the olive plant, and may contribute to the health benefits of olive fruit and leaves. There have been studies that measured the concentration of OeST1 (olive tree SULT1A1) in olive leaves. For example, a study published in the Journal of Agricultural and Food Chemistry in 2014 measured the expression levels of different sulfotransferase genes, including OeST1, in olive leaves using quantitative real-time polymerase chain reaction (qPCR) analysis. The study found that OeST1 was expressed at relatively high levels in olive leaves compared to other sulfotransferase genes. Another study published in the same journal in 2018 measured the activity of sulfotransferases, including OeST1, in olive leaf extracts using a radiolabeling assay. The study found that sulfotransferase activity in olive leaf extracts was mainly attributed to OeST1, and that its activity was higher in younger leaves compared to older ones. These studies suggest that OeST1 is present in significant amounts in olive leaves and is likely involved in the sulfation of various phenolic compounds in this plant tissue. However, it is important to note that the concentration of OeST1 or any other enzyme in olive leaves may vary depending on several factors, such as the cultivar, the growth conditions, and the age of the leaves. Therefore, further studies may be necessary to determine the concentration of OeST1 in different types of olive leaves and under different growth conditions.

It is understood that any plant the produces flavonoids or has minoxidil sulfotransferase enzymes, phenol sulfotransferase enzymes, and/or sulfotransferase enzymes can be used. Any of the methods and compositions can use the natural concentration of the enzyme found in the plant or an extract thereof. Further, any of the enzymes can be animal derived as well.

Table 1 shows results of a minoxidil response assay for each plant ingredient 8 uL diluted in 100 uL reaction tube incubated overnight. Results >0.4 means it has activity for minoxidil.

This method can involve obtaining a sample (e.g., plucked hairs having hair follicles, biopsy samples, etc.) from the subject. A colorimetric assay may be performed to measure a sulfotransferase enzyme activity in the sample, thereby generating an activity value indicative of the sulfotransferase activity level in the sample. The assay can involve placing the sample in a reaction mixture comprising an indicator dye and minoxidil. During the assay, the indicator dye undergoes a color change that correlates with the amount of sulfotransferase activity level in the sample, and wherein the activity value correlates with said color change. The activity value may be compared to one or more standardized activity values. Each standardized activity value can represent a degree of expected minoxidil response for hair re-growth or retention at a particular dosage and form of minoxidil.

As a non-limiting example, the sulfotransferase can be SULT1A1. The sample (e.g., 1 to n hair follicles) can be placed in a reaction mixture containing about 50 mM potassium phosphate buffer (pH approximately 6.5), about 5 mM magnesium chloride, about 20 µM adenosine 3',5'-diphosphate (PAP) or adenosine 3'-phosphate,5'-phosphosulfate (PAPS), about 5 mM p-nitrophenyl sulfate, and about 0.1 mM minoxidil. The reaction can take place in a transparent container with a lid or other opening in which the hair follicle samples may be inserted. The total amount of liquid

TABLE 1

Results of a minoxidil response assay for each plant ingredient

| Broccoli Powder | Spinach Powder | Kale | Grape Seed | Olive Leaf Powder | Cabbage Powder | Cherry Juice | Red Cabbage | Cauliflower Powder | Match Powder | Combination |
|---|---|---|---|---|---|---|---|---|---|---|
| 1.184 | 0.448 | 0.673 | 0.26 | 0.517 | 0.262 | 0.205 | 1.189 | 1.296 | 1.063 | 3.086 |

Exemplary Formulations

An exemplary formulation can include a composition comprising an alkalizing agent (1,000 mg of sodium bicarbonate) and a sulfotransferase enzyme (300 mg of Olea Europea Leaf Extract).

Another exemplary formulation can include a composition comprising alkalizing agents (375 mg of sodium bicarbonate+375 mg of potassium bicarbonate+150 mg of calcium (as calcium citrate/malate)+100 mg of magnesium (as magnesium aspartate)) and a sulfotransferase enzyme (500 mg of Minoxidil Sulfotrasnferase Enzyme Complex (*Olea europaea* L leaf, *Brassica napus*, *Brassica oleracea*, *Saccharina japonica*, *Oryza sativa*, *Brassica Oleracea*)). It is contemplated for this formulate to be administered twice daily.

Embodiments of the composition can include amounts of alkalizing agent ranging from 1%-100% by weight and/or amounts of sulfotransferase enzyme ranging from 1%-100% by weight. These amounts can induce the scalp SULT1A1 enzyme and subsequently increase minoxidil response.

Method of Quantifying Activity of SULT1A1

Embodiments can further relate to methods of determining or quantifying the activity of SULT1A1 in dermal papillae cells and/or dermal sheath. This can be done to determine whether and to what degree a subject would benefit from the treatments disclosed herein, and in particular treatments to increase, improve, or enhance minoxidil response. The method can involve using sulfotransferase activity results from a colorimetric assay, for example, to predict minoxidil response—e.g., SULT1A1 activity may be used as an indicator of minoxidil response.

in the assay container can be about 0.2 ml. As part of the above reaction, it is understood that in the presence of minoxidil sulfotransferase activity, p-nitrophenyl sulfate is converted to the colorimetric p-nitrophenol. The reaction may be mixed and then incubated for approximately 4 to 16 hours at 37° C. depending on the number of hair follicles used in the assay. Mixing may be by any mixing means known in the art—e.g., mechanical mixing, magnetic mixing, acoustic mixing, etc. The more hair follicles can result in less incubation time—e.g., an assay that uses one hair follicle may be incubated for approximately 16 hours, whereas an assay that uses two hair follicles may be incubated for approximately 4 hours.

After sample incubation, the reaction can be stopped via the addition of about 1/10th volume of approximately 0.25 M Tris-HCl buffer, pH 8.7, and mixed. The pH may vary (e.g., between 8.5 to 9.0). The absorbance at about 405 nm may then be read with a spectrophotometer or compared to a reference color card with a range of intensities corresponding to minoxidil sulfotransferase activity. Subjects with a relatively high level of sulfotransferase activity will have a relatively strong colorimetric readout, resulting in a relatively significant color change. In comparison, subjects with a relatively low level of sulfotransferase activity will have a relatively weak colorimetric readout, and correspondingly a relatively minimal color change. Subjects with a strong colorimetric assay response would be expected to respond to minoxidil for hair re-growth or retention. Subjects with a weak colorimetric assay response would be expected to have a poor response to minoxidil.

It is understood that this minoxidil response test can be used to determine if, when, and o what degree a subject may benefit from any of the treatments disclosed herein. For instance, a subject with a low or poor minoxidil response, based on the diagnostic test, can use embodiments of the composition to improve, increase, or enhance their minoxidil response. In addition, the diagnostic test results can be used to determine an optimal treatment regime. This may include modifying the concentration and/or frequency of the treatment (which can include administration of the composition and/or minoxidil) to suit the subject's minoxidil sulfotransferase activity.

EXAMPLES

The following examples demonstrate results of testing embodiments of the composition and methods disclosed herein.

Example 1

In a study on 40 subjects, 20 subjects were using the 6% TRIS (oral) combined with 0.05% hSULT1A1 topical and 20 subjects were using a vehicle solution without TRIS and hS1ULT1A1. In the group using TRIS, 70% of subjects had an increase SULT1A1 activity compared to 0% in the vehicle group.

Example 2

In a study on 60 subjects, 30 subjects were using the 10% Sodium Bicarbonate (oral) combined with 0.05% hSULT1A1 topical and 30 subjects were using a vehicle solution. In the group using Sodium Bicarbonate and hSULT1A1, 68% of subjects had an increase SULT1A1 activity compared to 0% in the vehicle group.

Example 3

In a study on 24 subjects, 12 subjects were using Sodium Bicarbonate 500 mg (oral) daily combined with 0.5 mg hSULT1A1 and 12 subjects were using a placebo. In the group using Sodium Bicarbonate and hSULT1A1, 50% of subjects had an increase SULT1A1 activity compared to 0% in the vehicle group.

Example 4

In a study on 28 subjects, 14 subjects were using Sodium Bicarbonate 500 mg (oral) daily combined with OeST1 (olive tree SULT1A1 extract) and 14 subjects were using a placebo. In the group using Sodium Bicarbonate and OeST1 (olive tree SULT1A1), 60% of subjects had an increase SULT1A1 activity compared to 5% in the vehicle group.

Example 5

One dose ranging study included 20 subjects. It was discovered that oral sodium bicarbonate, calcium bicarbonate or magnesium bicarbonate in dosages less than 500 mg q.d. did induce the scalp SULT1A1 enzyme. Dosages exceeding 1,000 mg q.d. induced the scalp SULT1A1 enzyme in 18% of subjects, while dosages above 2,000 mg q.d. induced the scalp SULT1A1 enzyme in over 30% of subjects.

Example 6

Using an oral pill formulation comprising alkalizing agents (375 mg of sodium bicarbonate+375 mg of potassium bicarbonate+150 mg of calcium (as calcium citrate/malate)+100 mg of magnesium (as magnesium aspartate)) and a sulfotransferase enzyme (500 mg of Minoxidil Sulfotrasnferase Enzyme Complex (*Olea europaea* L leaf, *Brassica napus, Brassica oleracea, Saccharina japonica, Oryza sativa, Brassica Oleracea*)) with 60 subjects, 30 subjects were using the above pill formula and 30 subjects were using a placebo pill. In the group using the above pill formula, 77% of subjects had an increase in scalp SULT1A1 activity compared to 5% in the group using the placebo pill.

Example 7

Using the following formulation in Table 2, a study was conducted in which 2 pills were given twice a day for 7 days. Hairs were plucked at baseline and day 7. Hair minoxidil sulfotransferase activity was measured using the minoxidil response test. In Table 3 (results) OD designates the activity. The increase overall for the cohort was 720%.

TABLE 2

| Formulation | |
|---|---|
| Brocolli Powder (containing natural levels of minoxidil sulfotransferase enzymes) | 125 mg |
| Spinach Powder (containing natural levels of minoxidil sulfotransferase enzymes) | 125 mg |
| Kale (containing natural levels of minoxidil sulfotransferase enzymes) | 125 mg |
| Olive Leaf Powder (containing natural levels of minoxidil sulfotransferase enzymes) | 125 mg |
| Red Cabbage (containing natural levels of minoxidil sulfotransferase enzymes) | 125 mg |
| Cauliflower Powder (containing natural levels of minoxidil sulfotransferase enzymes) | 125 mg |
| Match Powder (containing natural levels of minoxidil sulfotransferase enzymes) | 125 mg |
| Sodium bicarbonate (containing natural levels of minoxidil sulfotransferase enzymes) | 500 mg |

TABLE 3

| Resuls | | | |
|---|---|---|---|
| | Patient | Result (OD) | Change Day 7 (%) |
| Baseline | Patient 1 | 0.001 | 1,000.00% |
| Post Treatmet | Patient 1 | 0.011 | |
| Baseline | Patient 2 | 0.026 | 269.23% |
| Post Treatmet | Patient 2 | 0.096 | |
| Baseline | Patient 3 | 0.001 | 5,400.00% |
| Post Treatmet | Patient 3 | 0.055 | |
| Baseline | Patient 4 | 0.262 | −69.85% |
| Post Treatmet | Patient 4 | 0.079 | |
| Baseline | Patient 5 | 0.045 | 202.22% |
| Post Treatmet | Patient 5 | 0.136 | |
| Baseline | Patient 6 | 0.206 | −40.78% |
| Post Treatmet | Patient 6 | 0.122 | |
| Baseline | Patient 7 | 0.014 | 264.29% |
| Post Treatmet | Patient 7 | 0.051 | |
| Baseline | Patient 8 | 0.087 | −51.72% |
| Post Treatmet | Patient 8 | 0.042 | |
| Baseline | Patient 9 | 0.013 | 653.85% |
| Post Treatmet | Patient 9 | 0.098 | |
| Baseline | Patient 10 | 0.015 | 400.00% |
| Post Treatmet | Patient 10 | 0.075 | |
| Baseline | Patient 11 | 0.081 | 72.84% |
| Post Treatmet | Patient 11 | 0.14 | |
| Baseline | Patient 12 | 0.01 | 540.00% |
| Post Treatmet | Patient 12 | 0.064 | |
| | | | 720.01% |

It should be understood that the disclosure of a range of values is a disclosure of every numerical value within that range, including the end points. It should also be appreciated that some components, features, and/or configurations may be described in connection with only one particular embodiment, but these same components, features, and/or configurations can be applied or used with many other embodiments and should be considered applicable to the other embodiments, unless stated otherwise or unless such a component, feature, and/or configuration is technically impossible to use with the other embodiment. Thus, the components, features, and/or configurations of the various embodiments can be combined together in any manner and such combinations are expressly contemplated and disclosed by this statement.

It will be apparent to those skilled in the art that numerous modifications and variations of the described examples and embodiments are possible considering the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof.

It should be understood that modifications to the embodiments disclosed herein can be made to meet a particular set of design criteria. Therefore, while certain exemplary embodiments of the compositions and methods of using and making the same disclosed herein have been discussed and illustrated, it is to be distinctly understood that the invention is not limited thereto but may be otherwise variously embodied and practiced within the scope of the following claims.

What is claimed is:

1. A method for improving, increasing, or enhancing hair re-growth of a subject suffering from alopecia, the method comprising:
orally administering a composition comprising an alkalizing agent and a sulfotransferase enzyme to a subject suffering from alopecia, thereby promoting sulfotransferase enzyme expression in an outer root sheath of a hair follicle of the subject.

2. The method of claim 1,
further comprising administering the composition further involves administering the composition topologically, via injection, or transdermally; and/or
administering the composition as a drug, a nutritional supplement, or a cosmetic.

3. The method of claim 1, further comprising:
administering the composition before, during, and/or after administration of minoxidil.

4. The method of claim 1,
the composition further comprises minoxidil.

5. The method of claim 1, wherein:
the alkalizing agent comprises one or more of a bicarbonate, citrate, a loop diuretic, MOPS, BES, TES, HEPES, DIPSO, TAPSO, Acetamidoglycine, POPSO, HEPPSO, HEPPS, Tricine, Tris (tromethamine), Glycinamide, Glycylglycine, Bicine, or TAPS.

6. The method of claim 1, wherein:
the sulfotransferase enzyme comprises a human sulfotransferase enzyme and/or a non-human sulfotransferase enzyme.

7. The method of claim 1, wherein:
the sulfotransferase enzyme comprises one or more of a carbohydrate sulfotransferase, a galactose-3-O-sulfotransferase, a heparan sulfate 2-O-sulfotransferase, a heparan sulfate 3-O-sulfotransferase, a heparan sulfate 6-O-sulfotransferase, a N-deacetylase/N-sulfotransferase, a tyrosylprotein sulfotransferase, an uronyl-2-sulfotransferase, an estrone sulfotransferase, a chondroitin 4-sulfotransferase, SULT1A1, SULT1A2, SULT1A3, SULT1A4, SULT1B1, SULT1C2, SULT1C3, SULT1C4, SULT1D1P, SULT1E1, SULT2A1, SULT2B1, SULT4A1, or SULT6B1.

8. The method of claim 1, wherein:
the composition contains natural levels or extracts of minoxidil sulfotransferase enzymes, natural levels or extracts of phenol sulfotransferase enzymes, and/or natural levels of extracts sulfotransferase enzymes derived from *Populus trichocarpa, Populus* x *canescens, Salix* sp., *Arabidopsis thaliana*, silver poplar (*Populus alba*), Simon's poplar (*Populus simonii*), *S. purpurea, P. tremuloides, I. polycarpa, P. nigra, Oryza sativa*, Salicaceae family, Poplars (*Populus* sp.), *Idesia polycarpa*, Japanese orange cherry, Potato (*Solanum tuberosum*), Cabbage (*Brassica rapa*), *Populus trichocarpa* (Black cottonwood), *Salix* Sp. (Willow tree), Cotton (*Gossypium*), *Olea europaea* L, *Brassica napus, Apium graveolens, Brassica oleracea, Saccharina japonica, Solanum tuberosum*, and/or Black cottonwood; and
the natural levels or extracts of minoxidil sulfotransferase enzymes, phenol sulfotransferase enzymes, and/or sulfotransferase enzymes are present in amounts ranging from 1%-100% by weight.

9. The method of claim 1, wherein:
the sulfotransferase enzyme comprises OeST1.

10. The method of claim 1, further comprising:
quantifying activity of SULT1A1 in dermal papillae cells and/or dermal sheath of the subject.

11. The method of claim 10, further comprising:
determining a dosage and/or treatment regimen for the composition based on the quantitative measurement of activity of SULT1A1 in dermal papillae cells and/or dermal sheath of the subject.

12. A method for improving, increasing, or enhancing minoxidil response to a subject suffering from alopecia, the method comprising:
performing the method of claim 1 while the subject is undergoing minoxidil treatment for the alopecia.

13. A method for increasing sulfotransferase enzyme activity in a scalp and/or a liver of a subject suffering from alopecia, the method comprising:
orally administering a composition comprising an alkalizing agent and a sulfotransferase enzyme to a subject suffering from alopecia, thereby promoting sulfotransferase enzyme expression in an outer root sheath of a hair follicle of the subject.

* * * * *